United States Patent [19]
Devine et al.

[11] Patent Number: 5,856,519
[45] Date of Patent: Jan. 5, 1999

[54] CHIRAL AUXILARY FOR STEREOSELECTIVE ALKYLATIONS

[75] Inventors: Paul N. Devine, Old Bridge; Richard M. Heid, Jr., East Brunswick; David M. Tschaen, Holmdel, all of N.J.

[73] Assignee: Merck & Co., Inc., Rahway, N.J.

[21] Appl. No.: 935,970

[22] Filed: Sep. 23, 1997

Related U.S. Application Data

[62] Division of Ser. No. 761,175, Dec. 6, 1996, Pat. No. 5,708,186.

[51] Int. Cl.$^6$ .................................................. C07D 295/16
[52] U.S. Cl. ........................ 548/571; 546/245; 564/123; 564/170; 564/201
[58] Field of Search ........................... 546/245; 548/571; 564/123, 170, 201

[56] References Cited

U.S. PATENT DOCUMENTS

| | | | |
|---|---|---|---|
| 4,192,892 | 3/1980 | Thorsell et al. | 564/170 X |
| 4,222,960 | 9/1980 | Wechsberg et al. | 564/170 X |
| 4,622,415 | 11/1986 | Forster et al. | 560/62 |
| 5,622,971 | 4/1997 | Winn et al. | 514/315 |

FOREIGN PATENT DOCUMENTS 5-294911  11/1993  Japan .

OTHER PUBLICATIONS

Koh, K., et al., J. of Organic Chem., vol. 59(16), pp. 4683–4686, 1994.

Larsen, R.D., et al., J. Am. Chem. Soc., vol. 111(19), pp. 7650–7653, 1989.

Koh, K., et al., Tetrahedron Letters, vol. 35(3), pp. 375–378, 1994.

Koh, K., et al., Tetrahedron Letters, vol. 34(28), pp. 4473–4476, 1993.

Devine, P.N., et al., Tetrahedron Letters, vol. 37(16), pp. 2683–2686, 1996.

Durst, T., et al., Tetrahedron Letters, vol. 33(45), pp. 6799–6802, 1992.

Terajima et al., Chemical Abstracts, 111:96967 (1989).

Ehrhart et al., Chemical Abstracts, 56:15362a–d (1962).

Takahashi et al., Chemical Abstracts, 120:216993 (1994).

Smith et al., Chemical Abstracts, 86:5104, (1977).

Adam et al., Synthesis, 1994, 6, 563–566.

Davis et al., J. Org. Chem., 1986, 51, 2402–2404.

Julia et al., Bull Soc. Chim. Fr., 1996, 133, 15–24.

Schurig et al., J. Organomet. Chem., 370 (1989) 81–96.

Toyooka et al., Heterocycles, 29(5), 1989, 975–978.

*Primary Examiner*—Fiona T. Powers
*Attorney, Agent, or Firm*—J. Antonio Garcia-Rivas; Valerie J. Camara; Mark R. Daniel

[57] ABSTRACT

This invention relates to a method for the stereoselective synthesis of a 2-aryloxycarboxylic acid using a chiral auxiliary to enhance the stereoselectivity of the alkylation of the α-halo acid with an aryloxy group.

1 Claim, No Drawings

CHIRAL AUXILARY FOR STEREOSELECTIVE ALKYLATIONS

This is a division of application Ser. No. 08/761,175 filed Dec. 6, 1996 now U.S. Pat. No. 5,708,186.

BACKGROUND OF THE INVENTION

During the development of a commercially viable asymmetric synthesis of a potent endothelin antagonist, a highly stereoselective synthesis of a key intermediate, a 2-aryloxycarboxylic acid needed to be developed. A variety of methods of general applicability have been worked out by Durst and Koh utilizing (R)-pantolactone as a chiral auxiliary. [See Koh, K.; Durst, T. *J. Org. Chem.* 1994, 59, 4683.] Pantolactone esters of racemic α-halo acids have been coupled to a variety of phenoxides. Diastereoselectivities ranging from 76–90% have been obtained in this fashion with the "S" stereochemistry predominating at the newly formed asymmetric center. The "R" stereochemistry can be obtained utilizing (S)-ethyl lactate as the chiral auxiliary although diastereoselectivities are significantly lowered in comparison to pantolactone (60–75%). [For other diastereoselective reactions utilizing pantolactone or ethyl lactate see: (a) Larsen, R. D.; Corley, E. G.; Davis, P.; Reider, P. J.; Grabowski, E. J. J. *J. Am. Chem. Soc.* 1989, 111, 7650. (b) Koh, K.; Ben, R. N.; Durst, T. *Tetrahedron Lett.* 1994, 35, 375. (c) Koh, K.; Ben, R. N.; Durst, T. *Tetrahedron Lett.* 1993, 34, 4473.] The reaction is also characterized by sluggish rates and moderate yields.

The instant invention relates to a highly stereoselective coupling reaction mediated with a pyrrolidine derived lactamide as a chiral auxiliary.

SUMMARY OF THE INVENTION

This invention relates to a method for the stereoselective synthesis of a 2-aryloxycarboxylic acid using a chiral auxiliary, such as a compound of formula I to enhance the stereoselectivity of the alkylation of the α-halo acid with an aryloxy group. The invention also relates to a novel compound of formula:

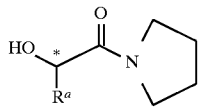

wherein: $R^a$ is $(C_1-C_6)$-alkyl, phenyl, or cyclohexyl, which is useful as a chiral auxiliary. Another aspect of this invention is a compound of formula:

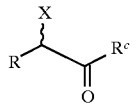

wherein:
X is Cl, Br, I, Omesylate, Otosylate, Otriflate;
$R^c$ is: a chiral auxiliary;
R is: $(C_1-C_6)$-alkyl, or aryl, wherein aryl is defined as phenyl or naphthyl, unsubstituted or substituted as defined hereinbelow.

DETAILED DESCRIPTION OF THE INVENTION

A method for the stereoselective preparation of a compound of formula:

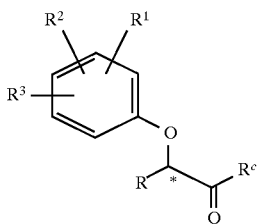

wherein:
* designates a stereogenic center;
$R^c$ is: a chiral auxiliary;
R is
  (a) $(C_1-C_6)$-alkyl,
  (b) aryl, wherein aryl is defined as phenyl or naphthyl unsubstituted or substituted with one, two or three substitutents defined as $R^4$, $R^5$ and $R^6$;
$R^1$, $R^2$, $R^3$, $R^4$, $R^5$ and $R^6$ are independently:
  (a) H,
  (b) F, Cl, Br, or I,
  (c) —$NO_2$,
  (d) —$NH_2$,
  (e) —NH($C_1-C_4$)-alkyl,
  (f) —N[($C_1-C_4$)-alkyl]$_2$,
  (g) —$SO_2NHR^7$,
  (h) —$CF_3$,
  (i) $(C_1-C_6)$-alkyl,
  (j) —$OR^7$,
  (k) —$S(O)_n$—$(C_1-C_4)$-alkyl,
  (l) —NHCO—$(C_1-C_4)$-alkyl,
  (m) —NHCO—$O(C_1-C_4)$-alkyl,
  (n) —$CH_2O$—$(C_1-C_4)$-alkyl,
  (o) —O—$(CH_2)_m$—$OR^7$,
  (p) —$CONR^7R^{12}$,
  (q) —$COOR^7$, or
  (r) —phenyl;
$R^4$ and $R^5$ on adjacent carbon atoms can be joined together to form a ring structure:

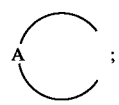

A represents:
  (a) —Y—$C(R^8)$=$C(R^9)$—,
  (b) —Y—$C(R^8)$=N—,
  (c) —Y—N=$C(R^8)$—,
  (d) —Y—$[C(R^{10})(R^{10})]_s$—Y—,
  (e) —Y—$C(R^8)(R^8)$—$C(R^8)(R^8)$—,
  (f) —$C(R^8)$=$C(R^9)$—Y—,
  (g) —N=$C(R^8)$—Y—,
  (h) —$C(R^{10})(R^{10})$—$C(R^{10})(R^{10})$—Y—, or
  (i) —$C(R^8)$=$C(R^9)$—$C(R^8)$=$C(R^9)$—;
n is 0, 1 or 2;
m is 2, 3 or 4;
s is 1 or 2;
Y is —O—, —$S(O)_n$— and —$N(R^{12})$—;
$R^7$ is:
  (a) H,
  (b) $(C_1-C_6)$-alkyl,
  (c) phenyl,
  (d) $(C_1-C_6)$-alkylphenyl, or
  (e) $(C_3-C_7)$-cycloalkyl;

$R^8$ and $R^9$ are independently:
(a) H,
(b) $(C_1-C_6)$-alkyl or $(C_2-C_6)$-alkenyl each of which is unsubstituted or substituted with one or two substituents selected from the group consisting of:
  i) —OH,
  ii) —O—$(C_1-C_4)$-alkyl,
  iii) —S(O)$_n$—$(C_1-C_4)$-alkyl,
  iv) —NR$^7$—$(C_1-C_4)$-alkyl,
  v) —NHR$^7$,
  vi) —COOR$^7$,
  vii) —CONHR$^7$,
  viii) —OCOR$^{12}$, or
  ix) —CONR$^7$R$^{12}$,
(c) $(C_3-C_7)$-cycloalkyl,
(d) F, Cl, Br, I,
(e) CF$_3$,
(f) —COOR$^7$,
(g) —CONR$^7$R$^{12}$,
(h) —NR$^7$R$^{12}$,
(i) —NR$^7$CONR$^7$R$^{12}$,
(j) —NR$^7$COOR$^{12}$,
(k) —SO$_2$NR$^7$R$^{12}$,
(l) —O—$(C_1-C_4)$-alkyl,
(m) —S(O)$_n$—$(C_1-C_4)$-alkyl, or
(n) —NHSO$_2$R$^{12}$;

$R^{10}$ is:
(a) H,
(b) $(C_1-C_4)$-alkyl unsubstituted or substituted with one of the following substituents:
  i) —OH,
  ii) —NR$^7$R$^{12}$,
  iii) —COOR$^7$,
  iv) —CONHR$^7$, or
  v) —CONR$^7$R$^{12}$, or
(c) Cl, or F;

$R^{12}$ is
(a) $(C_1-C_6)$-alkyl, unsubstituted or substituted with a substituent selected from the group consisting of:
  i) —OR$^7$,
  ii) —N[R$^7$]$_2$,
  iii) —NH$_2$,
  iv) —COOR$^7$,
  v) —N[CH$_2$CH$_2$]$_2$Q,
  vi) —CF$_3$, or
  vii) —CON(R$^7$)$_2$;
(b) aryl, wherein aryl is defined as phenyl or naphthyl which is unsubstituted or substituted with one or two substituents selected from the group consisting of:
  i) $(C_1-C_4)$-alkyl,
  ii) —O—$(C_1-C_4)$-alkyl,
  iii) —CO[NR$^7$]$_2$,
  iv) F, Cl, Br or I,
  v) —COOR$^7$,
  vi) —NH$_2$,
  vii) —NH[$(C_1-C_4)$-alkyl],
  viii) —N[$(C_1-C_4)$-alkyl]$_2$, or
  ix) —CON[CH$_2$CH$_2$]$_2$Q;
(c) —$(C_1-C_4)$-alkylaryl, wherein aryl is as defined above,
(d) $(C_3-C_7)$-cycloalkyl, (e)

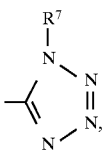

or
(f) CF$_3$;
R$^7$ and R$^{12}$ on the same nitrogen atom they can join together to form a ring selected from the group consisting of: morpholinyl, piperazinyl, or pyrrolyl, or
Q is O, S or —NR$^7$;
which comprises alkylating a halo derivative

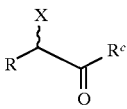

wherein X is Cl, Br, I, Omesylate, Otosylate or Otriflate; with an aryloxy derivative:

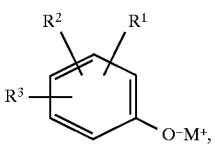

wherein M$^+$ is Na$^+$, K$^+$, Li$^+$, or N(R$^{16}$)$_4$+; and R$^{16}$ is H or $(C_1-C_6)$-alkyl;
in an organic solvent at a temperature range of about −60° C. to about 30° C. for about 30 minutes to about 30 hours to give an alkylated derivative bearing the chiral auxiliary:

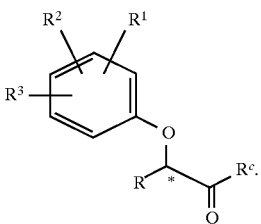

A method for the preparation of a compound of formula:

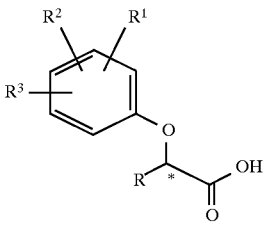

wherein:
* designates a stereogenic center;
R$^c$ is: a chiral auxiliary;
R is
(a) $(C_1-C_6)$-alkyl,
(b) aryl, wherein aryl is defined as phenyl or naphthyl unsubstituted or substituted with one, two or three substitutents defined as R$^4$, R$^5$ and R$^6$;

$R^1$, $R^2$, $R^3$, $R^4$, $R^5$ and $R^6$ are independently:
(a) H,
(b) F, Cl, Br, or I,
(c) —$NO_2$,
(d) —$NH_2$,
(e) —$NH(C_1-C_4)$-alkyl,
(f) —$N[(C_1-C_4)$-alkyl$]_2$,
(g) —$SO_2NHR_7$,
(h) —$CF_3$,
(i) $(C_1-C_6)$-alkyl,
(j) —$OR^7$,
(k) —$S(O)_n$—$(C_1-C_4)$-alkyl,
(l) —NHCO—$(C_1-C_4)$-alkyl,
(m) —NHCO—$O(C_1-C_4)$-alkyl,
(n) —$CH_2O$—$(C_1-C_4)$-alkyl,
(o) —O—$(CH_2)_m$—$OR^7$,
(p) —$CONR^7R^{12}$,
(q) —$COOR^7$, or
(r) -phenyl;
$R^4$ and $R^5$ on adjacent carbon atoms can be joined together to form a ring structure:

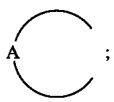

A represents:
(a) —Y—$C(R^8)$=$C(R^9)$—,
(b) —Y—$C(R^8)$=N—,
(c) —Y—N=$C(R^8)$—,
(d) —Y—$[C(R^{10})(R^{10})]_s$—Y—,
(e) —Y—$C(R^8)(R^8)$—$C(R^8)(R^8)$—,
(f) —$C(R^8)$=$C(R^9)$—Y—,
(g) —N=$C(R^8)$—Y—,
(h) —$C(R^{10})(R^{10})$—$C(R^{10})(R^{10})$—Y—, or
(i) —$C(R^8)$=$C(R^9)$—$C(R^8)$=$C(R^9)$—;
n is 0, 1 or 2;
m is 2, 3 or 4;
s is 1 or 2;
Y is —O—, —$S(O)n$— and —$N(R^{12})$—;
$R^7$ is:
(a) H,
(b) $(C_1-C_6)$-alkyl,
(c) phenyl,
(d) $(C_1-C_6)$-alkylphenyl, or
(e) $(C_3-C_7)$-cycloalkyl;
$R^8$ and $R^9$ are independently:
(a) H,
(b) $(C_1-C_6)$-alkyl or $(C_2-C_6)$-alkenyl each of which is unsubstituted or substituted with one or two substituents selected from the group consisting of:
i) —OH,
ii) —O—$(C_1-C_4)$-alkyl,
iii) —$S(O)_n$—$(C_1-C_4)$-alkyl,
iv) —$NR^7$—$(C_1-C_4)$-alkyl,
v) —$NHR^7$,
vi) —$COOR^7$,
vii) —$CONHR^7$,
viii) —$OCOR^{12}$, or
ix) —$CONR^7R^{12}$,
(c) $(C_3-C_7)$-cycloalkyl,
(d) F, Cl, Br, I,
(e) $CF_3$,
(f) —$COOR^7$,
(g) —$CONR^7R^{12}$,
(h) —$NR^7R^{12}$,
(i) —$NR^7CONR^7R^{12}$,
(j) —$NR^7COOR^{12}$,
(k) —$SO_2NR^7R^{12}$,
(l) —O—$(C_1-C_4)$-alkyl,
(m) —$S(O)_n$—$(C_1-C_4)$-alkyl, or
(n) —$NHSO_2R^{12}$;
$R^{10}$ is:
(a) H,
(b) $(C_1-C_4)$-alkyl unsubstituted or substituted with one of the following substituents:
i) —OH,
ii) —$NR^7R^{12}$,
iii) —$COOR^7$,
iv) —$CONHR^7$, or
v) —$CONR^7R^{12}$, or
(c) Cl, or F;
$R^{12}$ is
(a) $(C_1-C_6)$-alkyl, unsubstituted or substituted with a substituent selected from the group consisting of:
i) —$OR^7$,
ii) —$N[R^7]_2$,
iii) —$NH^2$,
iv) —$COOR^7$,
v) —$N[CH_2CH_2]_2Q$,
vi) —$CF_3$, or
vii) —$CON(R^7)_2$;
(b) aryl, wherein aryl is defined as phenyl or naphthyl which is unsubstituted or substituted with one or two substituents selected from the group consisting of:
i) $(C_1-C_4)$-alkyl,
ii) —O—$(C_1-C_4)$-alkyl,
iii) —$CO[NR^7]_2$,
iv) F, Cl, Br or I,
v) —$COOR^7$,
vi) —$NH_2$,
vii) —$NH[(C_1-C_4)$-alkyl],
viii) —$N[(C_1-C_4)$-alkyl$]_2$, or
ix) —$CON[CH_2CH_2]_2Q$;
(c) —$(C_1-C_4)$-alkylaryl, wherein aryl is as defined above,
(d) $(C_3-C_7)$-cycloalkyl,
or
(e)

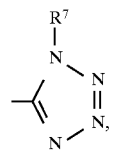

(f) $CF_3$;
$R^7$ and $R^{12}$ on the same nitrogen atom they can join together to form a ring selected from the group consisting of: morpholinyl, piperazinyl, or pyrrolyl, or
Q is O, S or —$NR^7$;
comprising the steps of:
1) alkylating a halo derivative

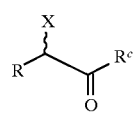

wherein X is Cl, Br, I, Omesylate, Otosylate or Otriflate; with an aryloxy derivative:

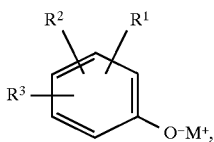

wherein $M^+$ is $Na^+$, $K^+$, $Li^+$, or $N(R^{16})_4+$; and $R^{16}$ is H or $(C_1–C_6)$-alkyl;
in an organic solvent at a temperature range of about –60° C. to about 30° C. for about 30 minutes to about 30 hours to give an alkylated derivative bearing the chiral auxiliary:

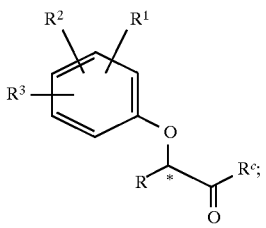

and 2) hydrolyzing the chiral auxiliary of the alkylated derivative with an inorganic base and peroxide in an aqueous solvent mixture to give a salt of the acid:

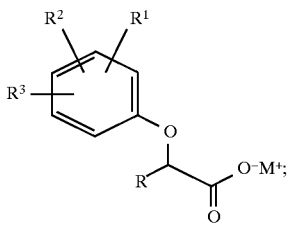

and wherein $M^+$ is $Na^+$, $K^+$, or $Li^+$;

3) neutralizing the salt of the acid with an acidic solution to give an acid:

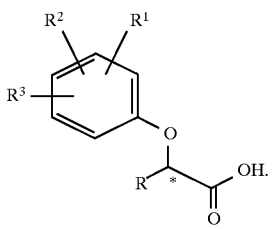

The alkylation step can be carried out in organic solvents such as tetrahydrofuran, toluene, xylenes, or dimethylforamide. The alkylation step requires the addition of a solution of the salt of the phenoxide generally prepared by the addition of the salt of t-butoxide to a tetrahydrofuran solution of the phenol. Phenoxide salts having counterions, such as potassium, sodium, lithium or ammonium $[N(R^{16})_4+$, where $R^{16}$ is defined as H or $(C_1–C_6)$-alkyl], are useful in this alkylation step. Thus, the organic solvent is often a mixture of, for example, tetrahydrofuran and t-butanol. The preferred temperature range for the alkylation step is 60° C. to about room temperature (25° C.).

The hydrolysis step can be carried out using an inorganic base, such as LiOH, KOH, NaOH, $KOCH_3$, $NaOCH_3$, $LiOCH_3$, $KOC_2H_5$, $NaOC_2H_5$, $LiOC_2H_5$, etc. The hydrolysis step also requires the presence of a peroxide such as hydrogen peroxide. The aqueous solvent mixtures useful in the hydrolysis step are tetrahydrofuran-water, toluene-water, dimethylformamide-water or alternatively a polar organic solvent such as methanol, ethanol, or t-butanol.

An acidic solution, such as saturated ammonium chloride solution is useful in the neutralization step.

A chiral auxilary is defined as an easily removable chiral group which is attached at a position near the site of alkylation and is capable of influencing the direction of nucleophilic attack. Some of the chiral auxiliaries useful in this method are:

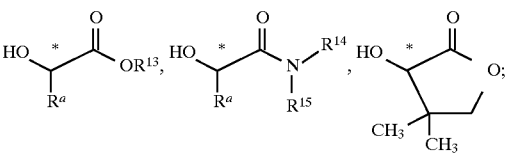

wherein:

$R^a$ is $(C_1–C_6)$-alkyl, phenyl, or cyclohexyl;

$R^{13}$ is $(C_1–C_6)$-alkyl, phenyl or cyclohexyl;

$R^{14}$ and $R^{15}$ are independently: $(C_1–C_{10})$-alkyl; or $R^{14}$ and $R^{15}$ can join together to form a 5- or 6-membered heterocyclic ring selected from the group consisting of: piperadinyl or pyrrolidinyl.

A preferred chiral auxiliary useful in this invention wherein $R^c$ is

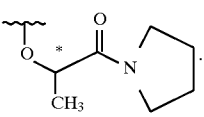

An aspect of this invention is a compound of formula:

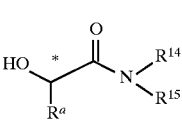

wherein:

$R^a$ is $(C_1–C_6)$-alkyl, phenyl or cyclohexyl; and $R^{14}$ and $R^{15}$ are independently: $(C_1–C_{10})$-alkyl or $R^{14}$ and $R^{15}$ can join together to form a 5- or 6-membered heterocyclic ring selected from the group consisting of piperadinyl or pyrrolidinyl.

Another aspect of this invention is a compound of formula:

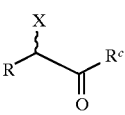

wherein:

X is Cl, Br, I, Omesylate, Otosylate, Otriflate;

$R^c$ is: a chiral auxiliary;

R is:

(a) $(C_1–C_6)$-alkyl, (b) aryl, wherein aryl is defined as phenyl or naphthyl unsubstituted or substituted with one, two or three substitutents defined as $R^4$, $R^5$ and $R^6$;

$R^4$, $R^5$ and $R^6$ are independently:

(a) H, (b) F, Cl, Br, or I,
(c) —$NO_2$,
(d) —$NH_2$,
(e) —$NH(C_1-C_4)$-alkyl,
(f) —$N[(C_1-C_4)$-alkyl$]_2$,
(g) —$SO_2NHR^7$,
(h) —$CF_3$,
(i) $(C_1-C_6)$-alkyl,
(j) —$OR^7$,
(k) —$S(O)_n$—$(C_1-C_4)$-alkyl,
(l) —NHCO—$(C_1-C_4)$-alkyl,
(m) —NHCO—$O(C_1-C_4)$-alkyl,
(n) —$CH_2O$—$(C_1-C_4)$-alkyl,
(o) —O—$(CH_2)_m$—$OR^7$,
(p) —$CONR^7R^{12}$,
(q) —$COOR^7$, or
(r) -phenyl, $R^4$ and $R^5$ on adjacent carbon atoms can be joined together to form a ring structure:

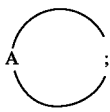

A represents:
(a) —Y—$C(R^8)$=$C(R^9)$—,
(b) —Y—$C(R^8)$=N—,
(c) —Y—N=$C(R^8)$—,
(d) —Y—$[C(R^{10})(R^{10})]_s$—Y—,
(e) —Y—$C(R^8)(R^8)$—$C(R^8)(R^8)$—,
(f) —$C(R^8)$=$C(R^9)$—Y—,
(g) —N=$C(R^8)$—Y—,
(h) —$C(R^{10})(R^{10})$—$C(R^{10})(R^{10})$—Y—, or
(i) —$C(R^8)$=$C(R^9)$—$C(R^8)$=$C(R^9)$—;

n is 0, 1 or 2;
m is 2, 3 or 4;
s is 1 or 2;
Y is —O—, —$S(O)_n$— and —$N(R^{12})$—;
$R^7$ is:
(a) H,
(b) $(C_1-C_6)$-alkyl,
(c) phenyl,
(d) $(C_1-C_6)$-alkylphenyl, or
(e) $(C_3-C_7)$-cycloalkyl;

$R^8$ and $R^9$ are independently:
(a) H,
(b) $(C_1-C_6)$-alkyl or $(C_2-C_6)$-alkenyl each of which is unsubstituted or substituted with one or two substituents selected from the group consisting of:
  i) —OH,
  ii) —O—$(C_1-C_4)$-alkyl,
  iii) —$S(O)_n$—$(C_1-C_4)$-alkyl,
  iv) —$NR^7$—$(C_1-C_4)$-alkyl,
  v) —$NHR^7$,
  vi) —$COOR^7$,
  vii) —$CONHR^7$,
  viii) —$OCOR^{12}$, or
  ix) —$CONR^7R^{12}$,
(c) $(C_3-C_7)$-cycloalkyl,
(d) F, Cl, Br, I,
(e) $CF_3$,
(f) —$COOR^7$,
(g) —$CONR^7R^{12}$,
(h) —$NR^7R^{12}$,
(i) —$NR^7CONR^7R^{12}$,
(j) —$NR^7COOR^{12}$,
(k) —$SO_2NR^7R^{12}$,
(l) —O—$(C_1-C_4)$-alkyl,
(m) —$S(O)_n$—$(C_1-C_4)$-alkyl, or
(n) —$NHSO_2R^{12}$;

$R^{10}$ is:
(a) H,
(b) $(C_1-C_4)$-alkyl unsubstituted or substituted with one of the following substituents:
  i) —OH,
  ii) —$NR^7R^{12}$,
  iii) —$COOR^7$,
  iv) —$CONHR^7$, or
  v) —$CONR^7R^{12}$, or
(c) Cl, or F;

$R^{12}$ is
(a) $(C_1-C_6)$-alkyl, unsubstituted or substituted with a substituent selected from the group consisting of:
  i) —$OR^7$,
  ii) —$N[R^7]_2$,
  iii) —$NH_2$,
  iv) —$COOR^7$,
  v) —$N[CH_2CH_2]_2Q$,
  vi) —$CF_3$, or
  vii) —$CON(R^7)_2$;
(b) aryl, wherein aryl is defined as phenyl or naphthyl which is unsubstituted or substituted with one or two substituents selected from the group consisting of:
  i) $(C_1-C_4)$-alkyl,
  ii) —O—$(C_1-C_4)$-alkyl,
  iii) —$CO[NR^7]_2$,
  iv) F, Cl, Br or I,
  v) —$COOR^7$,
  vi) —$NH_2$,
  vii) —$NH[(C_1-C_4)$-alkyl],
  viii) —$N[(C_1-C_4)$-alkyl$]_2$, or
  ix) —$CON[CH_2CH_2]_2Q$;
(c) —$(C_1-C_4)$-alkylaryl, wherein aryl is as defined above,
(d) $(C_3-C_7)$-cycloalkyl,

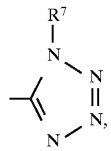

or (e)
(f) $CF_3$;

$R^7$ and $R^{12}$ on the same nitrogen atom they can join together to form a ring selected from the group consisting of: morpholinyl, piperazinyl, or pyrrolyl; and Q is O, S or —$NR^7$.

An embodiment of this aspect of the invention is a compound of formula:

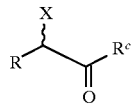

wherein:

$R^c$ is selected from the group consisting of:

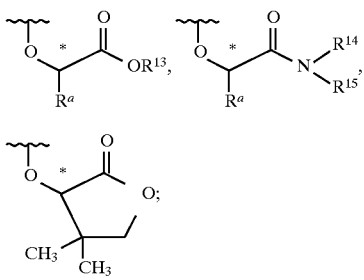

$R^a$ is $(C_1-C_6)$-alkyl, phenyl or cyclohexyl;
$R^{13}$ is $(C_1-C_6)$-alkyl, phenyl or cyclohexyl; and
$R^{14}$ and $R^{15}$ are independently: $(C_1-C_{10})$-alkyl, or $R^{14}$ and $R^{15}$ can join together to form a 5- or 6-membered heterocyclic ring selected from the group consisting of piperadinyl or pyrrolidinyl.

Another embodiment of this aspect of the invention is a compound of formula:

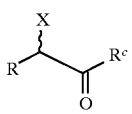

wherein:
X is Br or I;
$R^c$ is:

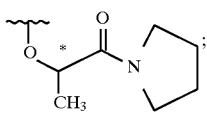

and
R is ethyl, phenyl or 3,4-methylenedioxyphenyl.

The alkyl substituents recited above denote straight and branched chain hydrocarbons of the length specified such as methyl, ethyl, isopropyl, isobutyl, neopentyl, isopentyl, etc.

The alkenyl-substituents denote alkyl groups as described above which are modified so that each contains a carbon to carbon double bond such as vinyl, allyl and 2-butenyl.

Cycloalkyl denotes rings composed of 3 to 8 methylene groups, each of which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl or quinolinyl.

The lactamide chiral auxiliary is synthesized from (R)- or (S)-ethyl lactate under Weinreb amidation conditions employing trimethylaluminum and pyrrolidine. [See (a) Nahm, S.; Weinreb, S. M. *Tetrahedron Lett.* 1981, 22, 3815. (b) Basha, A.; Lipton, M.; Weinreb, S. M. *Tetrahedron Lett.* 1977, 28, 4171.] The reaction is complete in less than 2 hours with no detectable loss in the enantiopurity. The product is obtained in 80% yield with the lactamide formed being suitable for use without further purification. The lactamide esters of the racemic α-halo acids were prepared via DCC coupling with commercially available acids or upon reaction with commercially available acid halides according to literature procedure. [See (a) Durst, T.; Koh, K. *Tetrahedron Lett.* 1992, 33, 6799. (b) Harpp, D. N.; Bao, L. Q.; Black, C. J.; Gleason, J. G.; Smith, R. A.; *J. Org. Chem.* 1975, 40, 3420.]

The coupling reaction was conducted by adding a preformed solution of aryloxide to a THF solution of halide, with or without tricaprylmethylammonium iodide, at the desired temperature (Table 1). The reactions were found to proceed at a much faster rate than with conventional ester auxiliaries. A reaction performed at −35° C. with sodium 4-methoxyphenoxide was completed in 0.5 h with a diastereoselectivity of 92% (entry 1). A similar reaction utilizing ethyl lactate as the auxiliary required a reaction time of 24 h at 0° C. Product was also obtained with a diminished diastereoselectivity of 60%. This observation also holds true for the ethyl lactate auxiliary. The fact that coupling reactions involving pyrrolidine lactamide auxiliaries proceed at a more rapid rate than their ester counterparts allows for the use of alternative phenoxide salts.

TABLE 1

| Entry | Temp (°C.) | Metal (M⁺) | X  | Time (h) | Yield (%) | DR** |
|-------|-----------|-----------|----|----------|-----------|------|
| 1     | −35       | Na        | Br | 0.5      | 78        | 96:4 |
| 2*    | −35       | Na        | Br | 0.5      | 84        | 95:5 |
| 3     | RT        | Li        | Br | 6        | 83        | 94:6 |
| 4     | 0         | Li        | Br | 8        | 80        | 95:5 |
| 5     | −15       | Li        | Br | 24       | 82        | 95:5 |
| 6*    | RT        | Li        | Br | 6        | 79        | 95:5 |
| 7*    | 0         | Li        | Br | 8        | 83        | 95:5 |
| 8*    | −15       | Li        | Br | 24       | 86        | 96:4 |
| 9     | RT        | Li        | I  | 0.25     | 87        | 98:2 |
| 10    | 0         | Li        | I  | 0.5      | 89        | 99:1 |

*Reaction conducted in the presence of 20 mol % tricaprylmethyl-ammonium iodide.
**Diastereomeric ratios determined via HPLC utilizing a Chiracel OD column and via 300 MHz ¹H NMR integration of the diastereomeric methyl doublets.

Lithium 4-methoxyphenoxide, although unreactive at −35° C., readily undergoes reaction with the α-bromoester at temperatures ranging from −15° C. to ambient (entries 3–6). No temperature effect is observed, with diastereoselectivities obtained at room temperature rivaling those obtained with the sodium salt at −35° C. (entries 6–8). However, conducting the coupling reaction utilizing the α-iodoester leads to significant increases in diastereoselection (entries 9

& 10). [The α-iodoester was prepared by treating the α-bromoester with NaI in acetone.] Reactions performed at ambient temperature and 0° C. showed enhanced diastereomeric ratios of 98:2 and 99:1 respectively.

The generality of the reaction was assessed by studying a variety of diastereomeric halides and substituted phenols (Table 2).

TABLE 2

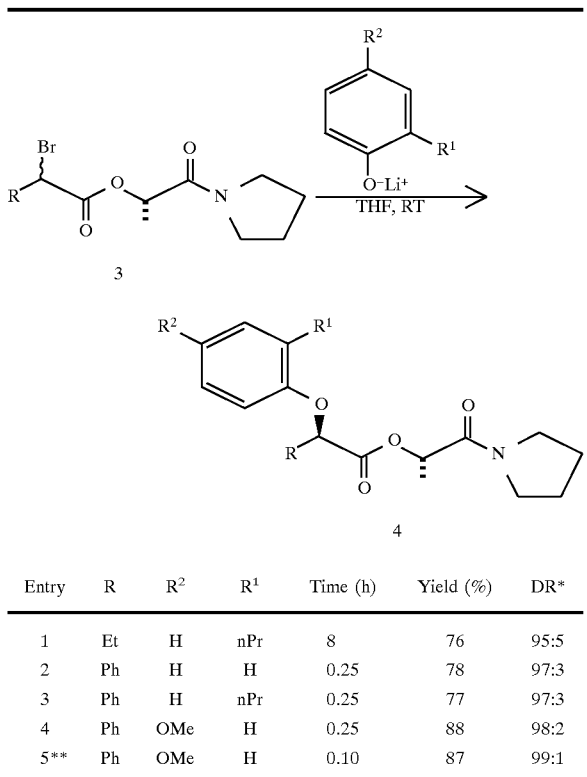

| Entry | R | $R^2$ | $R^1$ | Time (h) | Yield (%) | DR* |
|---|---|---|---|---|---|---|
| 1 | Et | H | nPr | 8 | 76 | 95:5 |
| 2 | Ph | H | H | 0.25 | 78 | 97:3 |
| 3 | Ph | H | nPr | 0.25 | 77 | 97:3 |
| 4 | Ph | OMe | H | 0.25 | 88 | 98:2 |
| 5** | Ph | OMe | H | 0.10 | 87 | 99:1 |

*Diastereomeric radio (DR) determined via HPLC utilizing either a Supelcosil LC CN column or a Chiracel OD column. Diastereoselectivities could also be obtained via 300 MHz $^1$H NMR.
**Reaction conducted utilizing the α-iodoester.

The substitution pattern about the phenol has minimal influence on the diastereoselectivity of the reaction. The sterically demanding 2-propylphenol gives similar diastereomeric ratios to unencumbered phenols (entries 1, 2-4). Again, diastereoselectivities observed are on the order of 5–15% higher than those obtained utilizing either ethyl lactate or pantolactone as the chiral auxiliary. Diastereomeric ratios of 99:1 can be obtained at room temperature through utilization of the α-iodoester (entry 5). The reaction is complete upon addition of the phenoxide and excellent yields are obtained.

The absolute configuration of the newly formed stereogenic center was determined by first hydrolyzing the coupled product to remove the chiral auxiliary, followed by converting the acid to the corresponding R- or S- methyl mandelate. [See Corey, E. J.; Link, J. O. *Tetrahedron Lett.* 1992, 33, 3431.]

The instant invention can be understood further by the following examples, which do not constitute a limitation of the invention.

EXAMPLE 1

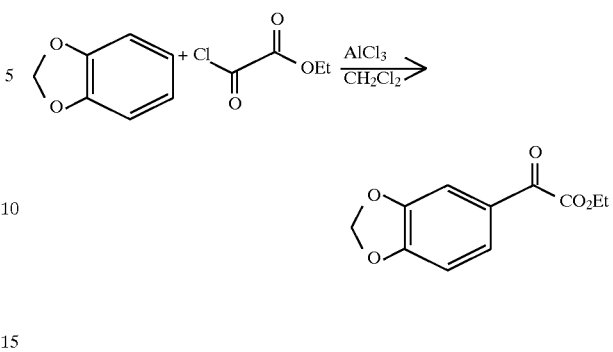

To a slurry of aluminum chloride (150 g, 1.13 mole) in methylene chloride (800 ml) at –55° C. was added ethyl oxalyl chloride (100 ml, 0.89 moles) over 5 min. The reaction exothermed to –48° C. and was cooled back down to –55° C. over 15 min. 1,3-Benzodioxole (100 g, 94 ml, 0.82 moles) was added over 15 min while the reaction temperature was maintained between –45° C. and –55° C. using dry ice/acetone. The red solution was aged for 20 min. The batch was carefully quenched into 700 ml of ice water and the mixture agitated for 10 min. The layers were separated and the organic layer was washed with water (500 ml). Concentration in vacuo provided the product as a brown oil (184 g) which was used in the next step without purification.

EXAMPLE 2

Synthesis of Ketoacid

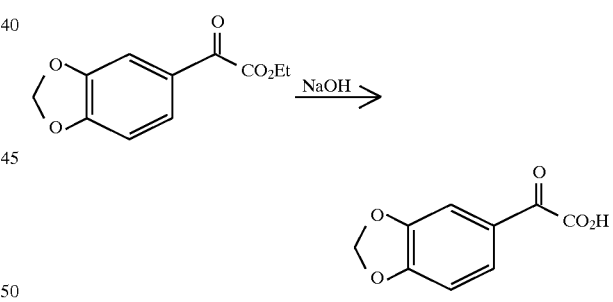

To a solution of ketoester 3 (182 g, 0.82 mole) in methanol (800 ml) was added a mixture of 5N sodium hydroxide (300 ml) and water (300 ml) while maintaining the temperature below 35° C. using an ice bath. The batch was aged for 20 min. during which time a precipitate formed. Methylene chloride (500 ml) was added and the mixture was acidified to pH 3.0 using concentrated HCl. The layers were separated and the organic phase was concentrated in vacuo to 100 ml. Toluene (300 ml) was added and concentration was continued to a final volume of 300 ml. The resulting slurry was aged for 1 h and filtered. The wet cake was washed with hexane and air dried to provide 120 g of ketoacid as a tan solid.

EXAMPLE 3

Lactate Ester Formation

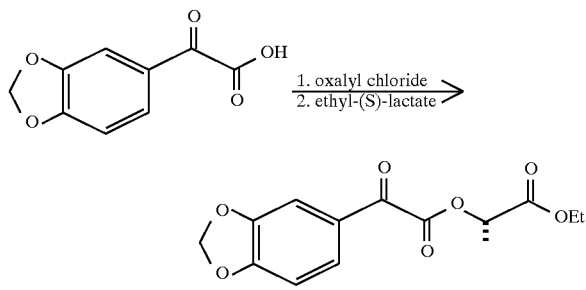

To a slurry of ketoacid (80 g, 0.41 moles) in methylene chloride (800 ml) at 20°–25° C. was added DMF (3 ml). Oxalyl chloride (37 ml, 0.42 moles, d=1.45 g/ml) was added over 10 min.

Within 20 min the reaction mixture turned to a clear solution. NMR assay of a small sample indicated <5% ketoacid remaining. The reaction mixture was then added via cannula over 15 min to a solution of ethyl-(S)-lactate (44 ml, 0.39 mole, d=1.042 g/ml), and TEA (143 ml, d=0.72 g/ml) in methylene chloride (600 ml) while maintaining the temperature <30° C. using an ice bath. The mixture was aged for 1 h. The batch was quenched into water (500 ml) and the layers separated. The organic layer was washed with water (500 ml) and then with sat'd sodium bicarbonate (2×300 ml). Concentration in vacuo provided 100 g of product as an oil. The material is used in the next step without purification.

EXAMPLE 4

Lactate ester Reduction

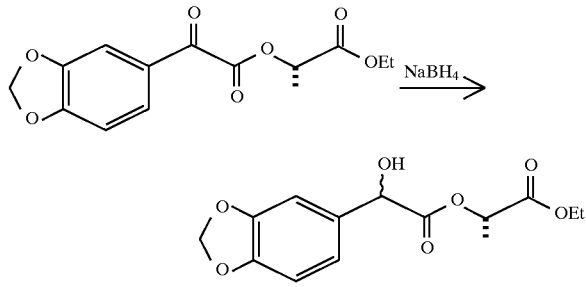

To a solution of lactate ester (100 g, 0.34 mole) in THF (600 ml) at 10°–15° C. was added water (65 ml). Sodium borohydride (5 g, 0.14 mole) was added in 5 portions over 25 min. The reaction temperature was maintained <25° C. using an ice bath. The mixture was aged for 20 min and poured into brine (300 ml) and ethyl acetate (600 ml). The layers were cut and the aqueous was back extracted with ethyl acetate (300 ml). The combined organic extracts were washed with water (200 ml) and the layers were separated. Concentration in vacuo yielded 100 g of product as an oil which was used in the next step without purification.

EXAMPLE 5

Preparation of Bromide

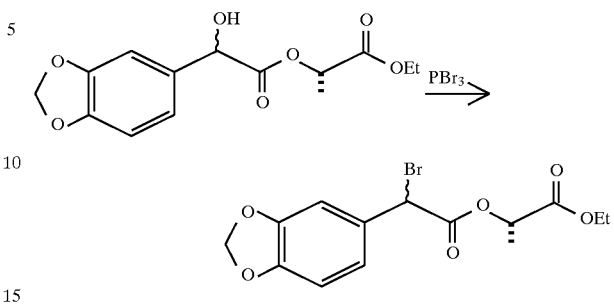

To a solution of the hydroxyester (100 g, 0.34 mole) in methylene chloride (500 ml) at 10°–15° C. was added phosphorous tribromide (12.8 ml, 0.13 moles, d=2.85 g/ml) over 5 min. The mixture was allowed to warm to 20° C. and aged for 1.5 h. The batch was quenched into water (250 ml) and the organic layer was washed with aqueous sodium bicarbonate (250 ml). Concentration of the organic layer in vacuo provided 111 g of bromide as a dark oil which was used in the next step without purification.

EXAMPLE 6

Phenoxide Coupling

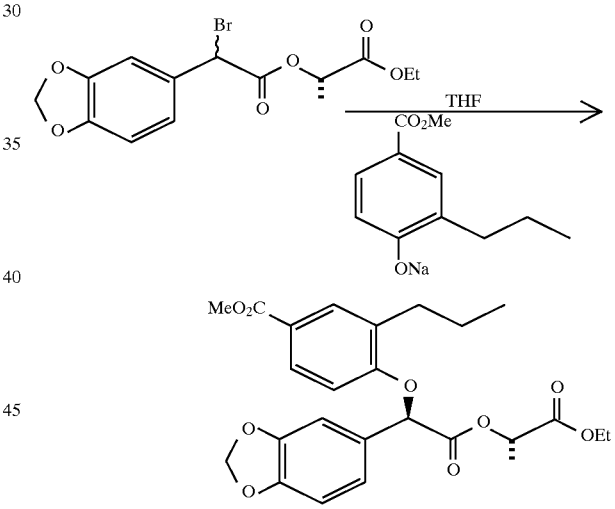

To a solution of methyl 4-hydroxy-3-n-propylbenzoate (23.7 g, 0.12 mole) in THF (175 ml) at 5°–10° C. was added sodium t-butoxide (11.7 g, 0.12 mole) in 3 portions over 15 min while maintaining the temperature <20° C. using an ice bath. The mixture was aged for 20 min and then added via a cannula to a solution of the bromide (55.0 g, 0.15 mole) in THF (400 ml) at −35° C. The reaction was aged at −35° C. for 20 h. The reaction was poured into a mixture of brine (200 ml), water (200 ml), and ethyl acetate (400 ml). The layers were cut and the organic layer was concentrated in vacuo to yield 69.0 g of product as an oil.

HPLC Assay

Column: Zorbax Rx-C8 4.6mm×25cm; Solvent: $CH_3CN:H_2O(0.1\%\ H_3PO_4)$ 60:40; Flow Rate: 1 ml/min; Wavelength: 220 nm; Column Temperature 25° C.; Retention Times: Major isomer: 20.2 min; Minor isomer:18.8 min; and bromide: 7.8 min.

EXAMPLE 7

Lactate Ester Hydrolysis

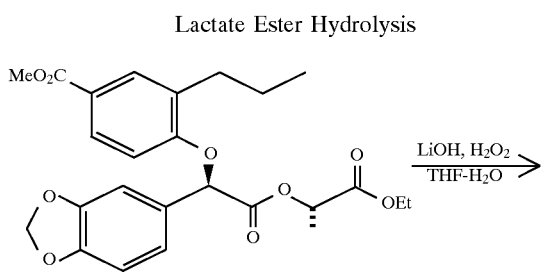

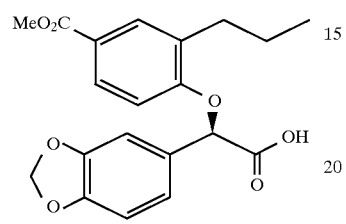

Hydrogen peroxide (3.5 l 133.8 mole) was added to a solution of lithium hydroxide (709 g, 16.9 mole) in water (3.5 l) and the mixture was aged for 20 min at 20°–25° C. This solution was then slowly added over 30 min to a cold (0°–5° C.) solution of lactate ester 8 (3.1 kg, 6.76 mole) in THF (28 l). The reaction mixture was aged for 30 min, cooled to 0°–5° C. and quenched with sated aqueous sodium bisulfite (6 l). Saturated aqueous ammonium chloride (4 l) and methyl t-butyl ether (36 l) was added and after agitation the layers were separated. The organic layer was dried over $MgSO_4$ (1 kg) and then concentrated in vacuo to yield 2.6 kg of crude product as a dark oil which was used without futher purification.

EXAMPLE 8

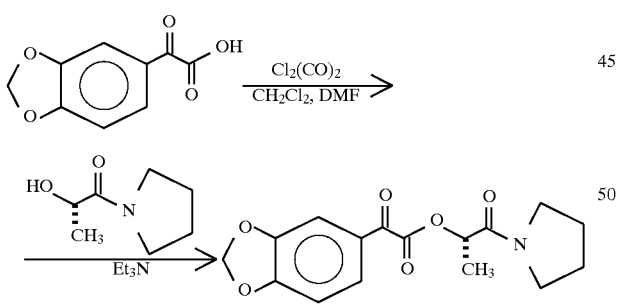

To a solution of the ketoacid (29.1 g) in methylene chloride (375 ml) was added 3 ml of DMF. Oxalyl-chloride (13.1 ml) was added dropwise and the mixture stirred for 30 minutes. The mixture was cooled to 0° C. and the hydroxya-mide (20.4 g) was added. Triethyl amine (42 ml) was added drowise and the mixture aged for 30 minutes. The reaction was quenched with water (200 ml) and the organic layer was washed with saturated sodium bicarbonate (200 ml), dried with $MgSO_4$ and concentrated to yield 44.4 g of product as an oil.

EXAMPLE 9

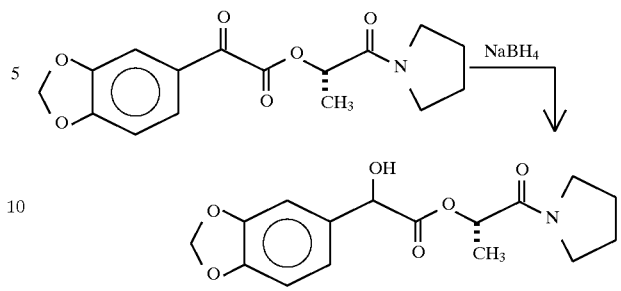

To a solution of ketoester (44.4 g) in THF (300 ml) was added in water (30 ml). Sodium borohydride (2.1 g) was added in portion over 15 minutes and the mixture was aged for 30 minutes. The reaction was quenched with brine (200 ml) and the phases separated. The aqueous phase was extracted with ethyl acetate and the combined organics were dried over $MgSO_4$ and concentrated to yield 44.4 g of the product as an oil.

EXAMPLE 10

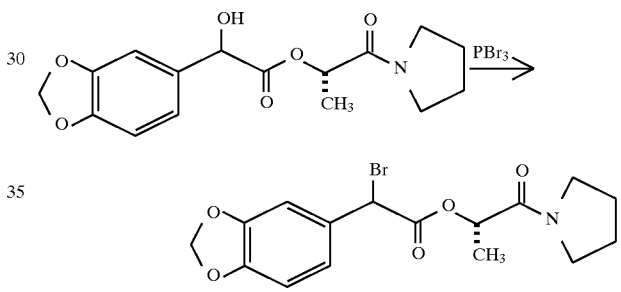

To a solution of alcohol (8.1 g) in methylene chloride (60 ml) at 0° C. was added $PBr_3$ (0.96 ml) over 5 minutes. The mixture was aged for 30 minutes and quenched with 50 ml of saturated sodium bicarbonated. The layers were separated and the aqueous was extracted with methylene chloride (100 ml). The combined organics were dried over $MgSO_4$ and concentrated to provide 7.3 g of product as an oil.

EXAMPLE 11

Phenoxide Coupling:

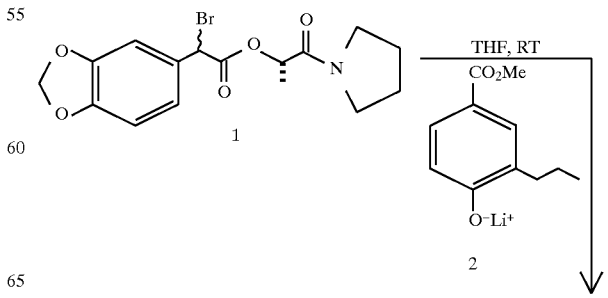

-continued

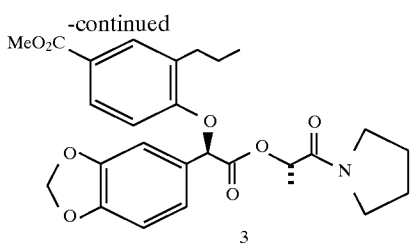

To a solution of methyl4-hydroxy-3-n-propylbenzoate (122 mg, 0.62 mmol) in THF (2 ml) at ambient temperature was added lithium t-butoxide (0.63 ml of a 1M solution, 0.63 mmol) in one portion. The lithium salt thus formed was added via cannula to a THF (3 ml) solution of bromide 1 (220 mg, 0.57 mmol). The reaction was stirred for 1 h at room temperature at which time HPLC assay indicated <1% bromide remaining. The reaction was quenched with water (10 ml) and EtOAc (10 ml) was added. The phases were separated and the aqueous phase was extracted with EtOAc (1×10 ml). The combined organic phases were washed with brine (1×10 ml) and concentrated in vacuo to give 290 mg of crude material. The product was isolated as a 98:2 mixture of diastereomers (determined by HPLC) and was used without further purification.

HPLC Assay:
Column: Supelcosil LC-CN 250 mm×4.6 mm; Solvent: Hexane:IPA 98:2; Flow rate: 1.0 ml/min; Wavelength: 220 nm; Column Temperature: 25° C.; Retention times: major isomer: 14.4 min; minor isomer: 17.2 min; and bromide: 13.2 min., 15.5 min.

EXAMPLE 12

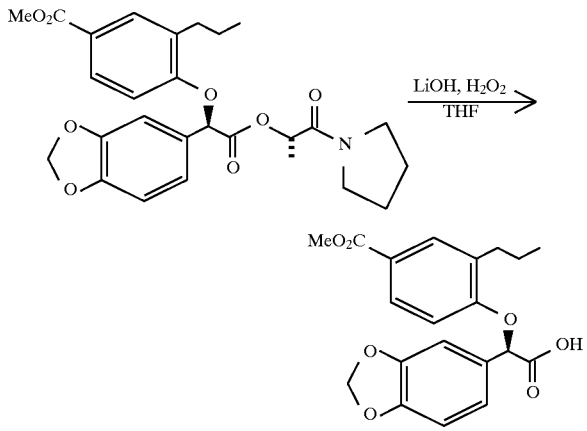

To a solution of 4.1 g of ester in 33 ml THF at 0° C. was added a mixture of 696 mg of LiOH and hydrogen peroxide (6.8 ml). The reaction was aged for 1 hour and quenched with 20 ml of saturated sodium bisulfite. The phases were separated and the aqueous phase was extracted with 50 ml $CH_2Cl_2$. The combined organic phase were dried over $MgSO_4$ and concentrated to yield 5.1 g of acid.

EXAMPLES 13–17

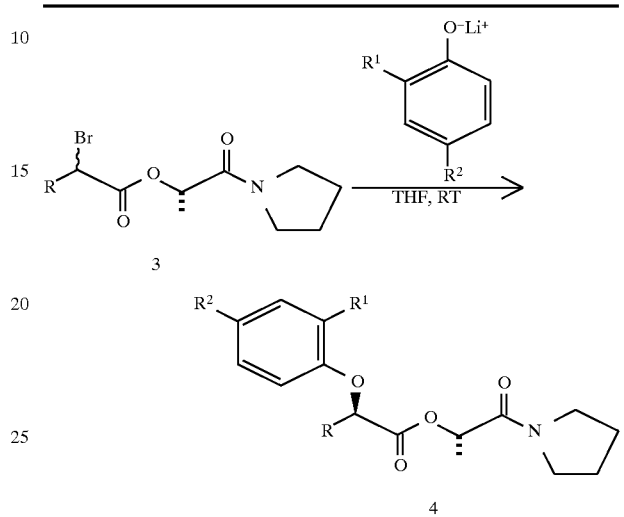

| Example | R  | $R^2$ | $R^1$ | Time (h) | Yield(%) | DR* |
|---------|----|----|----|----------|----------|------|
| 13      | Et | H  | nPr | 8        | 76       | 95:5 |
| 14      | Ph | H  | H   | 0.25     | 78       | 97:3 |
| 15      | Ph | H  | nPr | 0.25     | 77       | 97:3 |
| 16      | Ph | OMe | H  | 0.25     | 88       | 98:2 |
| 17†     | Ph | OMe | H  | 0.10     | 87       | 99:1 |

*Diastereomeric ratio (DR) determined via HPLC utilizing either a Supelcosil LC CN column or a Chiracel OD column. Diastereoselectivities could also be obtained via 300 MHz $^1$H NMR.
†Reaction conducted utilizing the α-iodoester.

Following the procedures described hereinabove the alkylated compound 4 (wherein R, $R^1$ and $R^2$ are as defined above), was prepared.

What is claimed is:
1. A compound of formula:

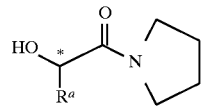

wherein $R^a$ is $(C_4-C_6)$-alkyl or cyclohexyl.

* * * * *